United States Patent
Tao et al.

(10) Patent No.: US 8,215,170 B2
(45) Date of Patent: Jul. 10, 2012

(54) CHEMICAL AND BIOLOGICAL SENSING USING TUNING FORKS

(75) Inventors: Nongjian Tao, Scottsdale, AZ (US); Salah Boussaad, Wilmington, DE (US)

(73) Assignee: Arizona Board of Regents, Scottsdale, AZ (US)

(*) Notice: Subject to any disclaimer, the term of this patent is extended or adjusted under 35 U.S.C. 154(b) by 1125 days.

(21) Appl. No.: 11/568,209

(22) Filed: Oct. 23, 2006

(65) Prior Publication Data
US 2007/0217973 A1    Sep. 20, 2007

Related U.S. Application Data

(60) Provisional application No. 60/569,907, filed on May 10, 2004.

(51) Int. Cl.
*G01N 29/12* (2006.01)
(52) U.S. Cl. ............ 73/579; 73/32 A; 73/24.01; 324/633
(58) Field of Classification Search ...... 73/24.01–24.06; 257/415–420; 422/58
See application file for complete search history.

(56) References Cited

U.S. PATENT DOCUMENTS

| | | | |
|---|---|---|---|
| 2,648,785 A | 8/1953 | Tournier | |
| 5,179,028 A | 1/1993 | Vali et al. | |
| 5,296,374 A | 3/1994 | Culshaw et al. | |
| 6,033,852 A | 3/2000 | Andle et al. | |
| 6,060,327 A | 5/2000 | Keen | |
| 6,598,459 B1 * | 7/2003 | Fu | 73/23.34 |
| 2002/0178787 A1 * | 12/2002 | Matsiev et al. | 73/24.01 |
| 2002/0179434 A1 * | 12/2002 | Dai et al. | 204/242 |
| 2003/0218467 A1 * | 11/2003 | Carlson et al. | 324/633 |

OTHER PUBLICATIONS

Boussaad et al., Polymer Wire Chemical Sensor Using a Microfabricated Tuning Fork, Jul. 24, 2003, American Chemical Society, Nano Letters vol. 3, No. 8, pp. 1173-1176.*
Guan, S., "Frequency Encoding of Resonant Mass Sensors for Chemical Vapor Detection", Anal. Chem., 75:4551-4557, 2003.
Guan, S. et al., "Rapid Scan Fourier Transform Detection of a Frequency Encoded Quartz Crystal Microbalance Array", Review of Scientific Instruments, 74(12):5241-5248, 2003.

* cited by examiner

*Primary Examiner* — In Suk Bullock
*Assistant Examiner* — Robert Eom
(74) *Attorney, Agent, or Firm* — George A. Leone; Citadel Patent Law (57) ABSTRACT

A device for sensing a chemical analyte is disclosed. The device is comprised of a vibrating structure having first and second surfaces and having an associated resonant frequency and a wire coupled between the first and second surfaces of the vibrating structure, wherein the analyte interacts with the wire and causes a change in the resonant frequency of the vibrating structure. The vibrating structure can include a tuning fork. The vibrating structure can be comprised of quartz. The wire can be comprised of polymer. A plurality of vibrating structures are arranged in an array to increase confidence by promoting a redundancy of measurement or to detect a plurality of chemical analytes. A method of making a device for sensing a chemical analyte is also disclosed.

7 Claims, 5 Drawing Sheets

TO ELECTRONIC
CIRCUIT

CHEMICAL AND BIOLOGICAL SENSING USING TUNING FORKS

CLAIM TO DOMESTIC PRIORITY

This application is a U.S. National Stage Application filed under 35 U.S.C. 371 claiming priority from the International Application No. PCT/US2005/016221, filed May 10, 2005, which claims priority to provisional application Ser. No. 60/569,907 entitled "Chemical and Biological Sensing Using Tuning Forks", filed on May 10, 2004, by Nongjian Tao.

STATEMENT REGARDING FEDERALLY-SPONSORED RESEARCH OR DEVELOPMENT

The U.S. Government has a paid-up license in the present invention and the right in limited circumstances to require the patent owner to license others on fair and reasonable terms as provided by the terms of Grant No. DE-FG03-01ER45943 awarded by the Department of Energy.

FIELD OF THE INVENTION

The present invention relates in general to chemical and biological sensors and, more particularly, to an apparatus and method of detecting chemical or biological analytes using a thin wire and microfabricated tuning forks.

BACKGROUND OF THE INVENTION

The ability to detect, quickly and reliably, the presence or absence of specific chemicals can be a matter of life or death. Leaks of toxic gases in air, monitoring of glucose in the bloodstream, testing for harmful compounds in foods and water, and early alert of chemical and biological warfare agents all require reliable and sensitive sensing devices. For example, the ability to detect, quickly and reliably, the presence of trace amounts of explosives or chemical and biological warfare agents in air is an urgent demand of homeland security.

Several detection devices and accompanying methods have been proposed and developed as part of a body of prior art. One example of a prior art sensor device is the quartz crystal microbalance. A quartz crystal microbalance is a disk-like quartz crystal. When an analyte (chemical or biological species) absorbs or binds onto the crystal surface, the effective mass of the crystal increases and results in a decrease in the resonance frequency that can be accurately measured. Using a quartz crystal microbalance, however, is subject to inherent limitations. Quartz crystal microbalance sensors detect changes in mass. By using a method to detect changes in mass, one cannot easily discriminate specific binding due to the analyte from nonspecific bindings due to other molecules. The smallest amount of mass change, a parameter that describes the sensitivity of a mass-detection based sensor, is also limited.

Another widely used mechanical device for chemical or biological sensors is the microfabricated cantilever, or microcantilever. Microcantilever sensors can be operated either in AC and DC modes. In AC mode, the cantilever is set to oscillate and the resonance frequency is detected upon binding of an analyte onto the cantilever surface. The operation of detecting the applicable resonance frequency of microcantilever sensors is similar to the detection operation performed using the quartz crystal microbalance. In the direct current (DC) mode, a bending in the cantilever induced by analyte adsorption is detected. The bending of the cantilever arises from analyte adsorption-induced surface stress in the cantilever.

Microcantilever sensors, like quartz crystal microbalance sensors, have inherent limitations. In both AC and DC modes, it is necessary to be able to detect the mechanical movement of the microcantilever, which is normally achieved in two ways, optical method and piezoresistive detection. The optical method requires the use of laser diodes and photodetectors in addition to the employment of complex electronic circuits. Mechanical adjustments of the laser beam and photodetectors is also required, which are not desirable for many practical devices. Piezoresistive detection uses a cantilever whose resistance is sensitive to mechanical bending. Piezoresistive detection allows for electrical detection of a mechanical response of the cantilever without using external optics. However, piezoresistive cantilevers have limited sensitivity and consume considerable amounts of power during operation. Moreover, scaling microcantilever sensors down to the nanometer scale remains a difficult task.

While many sensor devices and accompanying methods have been proposed and developed, a device that can, for example, cheaply and effectively satisfy the demands of homeland security has yet to be introduced due to a number of practical issues. A need exists for a power-efficient, stable and accurate apparatus and method to detect chemical and biological analytes.

SUMMARY OF THE INVENTION

In one embodiment, the present invention is a device for sensing a chemical analyte, comprising a vibrating structure having first and second surfaces and having an associated resonant frequency and a polymer wire coupled between the first and second surfaces of the vibrating structure, wherein the analyte interacts with the polymer wire and causes a change in the resonant frequency of the vibrating structure.

In another embodiment, the present invention is a device for sensing a chemical analyte, comprising a vibrating structure having first and second surfaces and having an associated resonant frequency and a wire coupled between the first and second surfaces of the vibrating structure, wherein the analyte interacts with the wire and causes a change in the resonant frequency of the vibrating structure.

In another embodiment, the present invention is a device for sensing a chemical analyte, comprising a vibrating structure having an associated resonant frequency and a coating disposed over a surface of the vibrating structure, wherein the analyte interacts with the coating and causes a change in the resonant frequency of the vibrating structure.

In another embodiment, the present invention is a method of manufacturing a device for sensing a chemical analyte, comprising providing a vibrating structure having first and second surfaces and having an associated resonant frequency and providing a wire coupled between the first and second surfaces of the vibrating structure, wherein the analyte interacts with the wire and causes a change in the resonant frequency of the vibrating structure.

In another embodiment, the present invention is a device for sensing a chemical analyte, comprising a first surface, a material having a second surface and an associated mechanical property, and a wire coupled between the first surface and the second surface, wherein the analyte interacts with the wire and causes a change in the mechanical property of the material.

DETAILED DESCRIPTION OF THE DRAWINGS

The present invention is described in one or more embodiments in the following description with reference to the Figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

A chemical and biological sensor device can be constructed which measures changes in the mechanical properties of a micro or nanowire upon binding or adsorption to an analyte. The sensor device and accompanying method of analysis serves to alleviate the limitations caused by use of previous sensor designs. Changes in mechanical properties of the wire can be sensitively detected by various means. The wire can be attached to or between surfaces of a vibrating structure. The vibrating structure can include such devices as mechanical resonators which can have an associated resonant frequency. The vibrating structure can include materials with piezoelectric properties, such as piezoelectric crystals which convert mechanical stresses to electrical charge. The vibrating structure can include any material which can be made to oscillate. A change in the mechanical property of an attached micro or nanowire causes a corresponding change in a mechanical property of the vibrating structure. A change in a mechanical property of the vibrating structure can then be measured and recorded.

Changes in mechanical properties in the wire can be measured simply by connecting the wire to a material which also has an associated mechanical property. Again, a change in the mechanical properties of the wire causes a measurable change in a mechanical property of the material.

For example, one can attach one end of the wire to a fixed object and the other end to material or vibrating structure commonly known as a microfabricated cantilever. The change in the mechanical stress of the wire causes a measurable deflection in the microcantilever (in the case of a material) or a measurable shift in the resonance frequency of the microcantilever (in the case of a vibrating structure). In addition to employing a microcantilever, any recognized mechanical resonator can be used which has an associated resonance frequency.

Another method of measuring changes in the mechanical properties of a micro or nanowire is to connect the wire to the two prongs of a commonly-obtained microfabricated tuning fork, another example of a vibrating structure. When the fork is set to oscillate (e.g., resonance frequency), the wire is stretched and compressed in each oscillation cycle. Changes in the mechanical properties due to analyte molecules can be detected as a shift in the frequency, phase, amplitude or the quality factor.

Figure 1A:
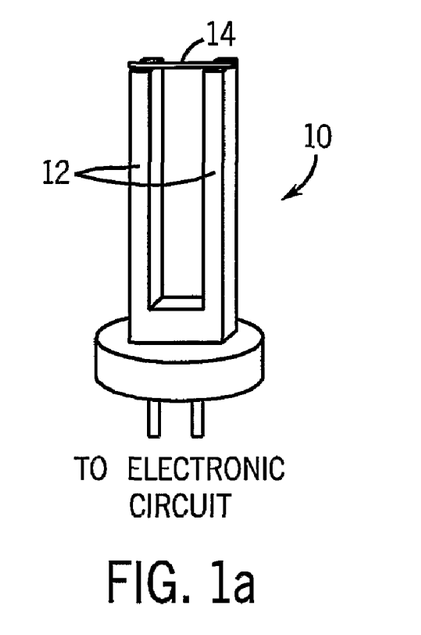
FIG. 1a illustrates a device for sensing a chemical analyte.

Turning to FIG. 1a, a microfabricated tuning fork 10 is shown. Tuning fork 10 can be composed of quartz. Quartz crystal tuning forks 10 are widely used for time-keeping devices, such as wrist watches. The use of quartz crystal tuning forks 10 revolutionized the watch industry in the 1970s. Billions of quartz tuning forks 10 are manufactured annually for time-keeping devices at a cost of a few cents each. Quartz tuning forks can be readily obtained from a myriad of commercial manufacturers such as ECS International, Inc. in Olathe, Kans. The widely available commercial quartz tuning fork 10 used in wristwatches is approximately two (2) millimeters long, approximately two-hundred (200) micrometers wide and approximately one-hundred (100) micrometers thick.

Fork 10 is stable due to the relatively rigid structure of tuning fork 10. Commercial quartz tuning forks 10 are well-packaged with convenient electrical wiring options. Referring to FIG. 1a, fork 10 is shown with an attached electrical contact which leads to an electrical circuit. The electrical circuits for driving and sensing the resonance of forks 10 have been optimized and miniaturized over years of research and development by the watch industry. Fork 10 is seen with associated electrical connections which lead to a respective electronic circuit.

Commercial quartz tuning forks 10 can achieve a force sensitivity of a few pN (1 Hz bandwidth), which is much smaller than the force required to break a single covalent bond. The extremely high force sensitivity of fork 10 makes fork 10 a preferable mechanism in Noncontact Atomic Force Microscopy to detect weak van der Waals forces.

Forks 10 which are composed of quartz have additional distinctive features which make them attractive for use in a chemical or biological sensor device. The quality factor (Q) of a quartz tuning fork 10 often exceeds ten-thousand (10,000) in air due to the superior properties of quartz crystals. The large quality factor, together with the noise cancellation mechanism of two identical prongs in the forks 10, results in extremely high force sensitivity with minimal power dissipation. Quartz tuning forks 10 are also astonishingly stable over time and temperature, which is the reason that the time deviation of even a cheap toy watch is no more than a few seconds a week.

Figure 1B:
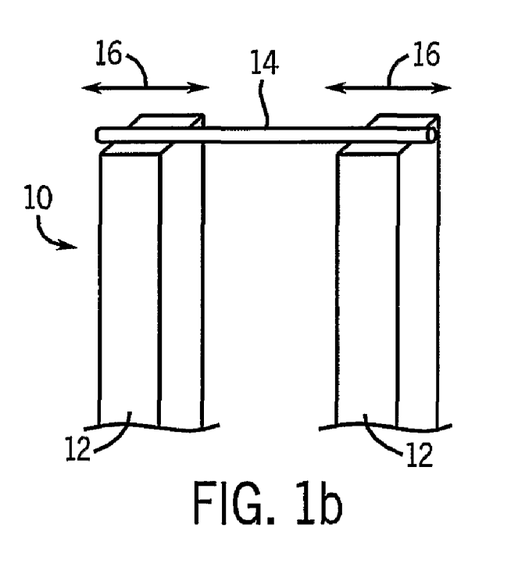
FIG. 1b illustrates an expanded view of a device for sensing a chemical analyte.

Referring again to FIG. 1a, micro or nanowire 14 is shown coupled to the end of prongs 12 of fork 10. An expanded illustration of fork 10 is depicted in FIG. 1b. Here, a view of prongs 12 is seen, with wire 14 attached to the upper end of prongs 12. Arrows 16 indicate the associated oscillation motion of each prong 12.

Wire 14 can be composed of a variety of materials which may be chosen for a specific application. Wire 14 can include metallic or polymeric materials. Wire 14 can include natural or man-made materials, or a combination of natural and man-made materials. In order to maximize specificity, one must either choose proper materials to make wire 14 or coat wire 14 with proper materials such that different analyte species interact with wire 14 in a way that is intended. For example, if Palladium (Pd) wire is used, the specific adsorption of hydrogen molecules can drastically change the mechanical properties of the Pd wires 14.

In another example, wires 14 can be composed of various polymer materials. Polymer materials have several advantages for chemical sensor applications. For example, polymer materials can be easily pulled into thin wires with a built-in stress, which can be used to amplify the signal when adsorption or binding of an analyte triggers a sudden release of the stress. In addition, polymer materials are highly porous, which allows analyte molecules to interact with the entire volume of a polymer wire 14 to yield a large response. Certain polymers are prone to swelling and degradation in an ambient environment, however. Choosing appropriate polymers that are stable under ambient conditions is one method to reduce the swelling and degradation problem. Another approach can be to design an appropriate housing of polymer wires 14.

Polymer wires 14 can be formed by pulling polymers which are dissolved in organic solvents or melted by heating. Polymer solutions can be obtained by dissolving various polymers in various solvents. Ethylcellulose polymers, butylcellulose polymers and wax made of high molecular petroleum hydrocarbons can be dissolved in toluene or absolute ethanol to obtain a polymer solution. Polyvinylphosphonic acid (PVPA) and polyacrylic acid (PAA) can be dissolved in deionized water to obtain a respective polymer solution. Commercial polymer mixtures and other conventional or unconventional materials can also be utilized to form wires 14.

Additional non-limiting examples of useful water soluble polymers which can be useful in forming wires 14 are polyvinyl pyrolidone (PVP) available from ISP in Wayne, N.J., hydroxyethylmethacrylate, vinylpyrrolidone polymers and copolymers, which can be selected from the group consisting of polyvinylpyrrolidone vinylpyrrolidone/dimethylaminoethyl methacrylate copolymer, vinyl caprolactam/vinylpyrrolidone/dimethylaminoethyl methacrylate terpolymer, vinylcaprolactam/vinylpyrroldone/dimethylaminopropyl methacrylamide terpolymer, vinylpyrrolidone/dimethylaminopropyl methacrylamide copolymer, vinylpyrrolidone/dimethylaminoethyl methacrylate copolymer, and quaternized derivatives. Additional examples include a solvent mixture of an aqueous solvent and a polar organic solvent where the polymer can be a member selected from the group consisting of hydroxyethylmethacrylate copolymer or terpolymer, or an associated derivative, where the copolymer or terpolymer can include at least one member of the group consisting of 2-hydroxyethylmethacrylate/co-acrylic acid copolymer, 2-hydroxyethylmethacrylate/methacrylic acid copolymer, 2-hydroxyethylmethacrylate/dimethylaminopropylmethacrylate, 2-hydroxyethylmethacrylate/dimethyl-aminoethylmethacrylate, and 2-hydroxyethylmethacrylate-vinylpyrrolidone, quaternized polyhydroxyethlymethacrylate-co-dimethylaminopropylmethacrylat, quaternized polyhydroxyethlymethacrylate-co-dimethylaminoethylmethacrylate, a guanidine polymer or a salt thereof, also termed a "polyguanidine" or a "polyhexylmethylbiguanidine".

Additional non-limiting examples of useful water insoluble polymers are fluorinatedethylenepropylene (FEP) and polytetrafluoroethylene (PTFE).

Polymer wires 14 can contain at least one cross-linker selected from group of polyamide-epichlorhydrin resin and polyfunctional aziridine or a mixture thereof. The first layer composition can contain an azetinidium compound, or salt thereof, as a polyamide-epichlorhyrin cross-linker. However, other crosslinkers can be used and are contemplated.

Polymer wires 14 can include a plasticizer which is a member selected from the group consisting of phosphates, substituted phthalic anhydrides, glycerols, and polyglycols. An example plasticizer is polyethylene glycol or a derivative. However, other plasticers may be used and are comtemplated.

Polymer wires 14 can include side chains containing specific binding sites. A non-limiting example is a polynucleic acid polymer containing a specificity for another polymer nucleic acid polymer sequence or protein sequence. Additional non-limiting examples of wires with specific binding moieties are avidin-streptavidin, monoclonal antibodies and ionic binding.

Polymer wires 14 can include additives such as antifoam agents, surfactants, dyestuffs, particles and associated mixtures.

Hydrophobic, hydrophilic, and a combination of hydrophobic and hydrophilic polymers can be used in wires 14. In addition, natural fibers such as cellulose and other similar materials can be used in the wires 14. Fibers from stimuli-sensitive polymers (SSPs) that respond to environmental changes such as pH, temperature, and electrolyte can be used in the wires 14. Techniques involving wet spinning of cross-linked gels made from SSP, coating existing fibers with cross-linked SSP using high intensity UV curing techniques and grafting SSPs to existing fibers using gamma radiation can be used in association with the formation of wires 14.

Polymer wires 14 can be formed at room temperature by pulling the polymer gels or viscous solutions of polymer according to the following procedure. As mentioned previously, ethylcellulose polymers, butylcellulose polymers and wax made of high molecular petroleum hydrocarbons can be dissolved in toluene or absolute ethanol to obtain a polymer solution. Polyvinylphosphonic acid (PVPA) and polyacrylic acid (PAA) can be dissolved in deionized water to obtain a respective polymer solution. Two small drops of polymer solution (0.1-1 microliter) can be placed on both prongs 12 of fork 10. Before the drops completely dry out, a hypothermic syringe needle can be dipped into one of the polymer drops located on a first prong 12 and pulled into the drop located on the second prong 12. The pulling drags a strand of polymer solution across the gap between the two prongs 12. The surface tension on the strand leads to capillary thinning and formation of a thin polymer wire 14. The diameter of a typical polymer wire 14 is between a few hundred nanometers to a few microns. The polymer wires can then be left in air to dry out before use.

Wires 14 may be manufactured by any commercial method known in the art. Traditionally in the semiconductor industry, wire bonding machines are used to connect extremely fine electrical wires to silicon chips. Wire bonding machines can be adapted to manufacture wires 14 and couple wires 14 to the ends of forks 10 using adapted methods generally known in the art, such as thermosonic ball and wedge bonding or ultra-sonic wedge bonding techniques.

In addition to bridging forks 10 with polymer wires 14, an alternative way of using polymers as sensor materials is to coat forks 10 with a thin layer of polymers. A drop (<0.35 microliters) of dilute polymer solution may be placed on the surface of prongs 12. Coating forks 10 with a thin layer of polymers can reduce sensitivity, but can be useful for polymers that cannot be easily stretched or pulled into thin wires 14. Additionally, forks 10 which are coated with proper polymer thin films can be particularly useful for monitoring relative humidity, which does not require high sensitivity.

As mentioned previously, when a polymer wire 14 is solidified, a large mechanical stress is built in the wire, which can be released upon binding or adsorption of a respective chemical or biological analyte species. Optimal sensitivity can also be achieved by optimizing the geometry of the wires, which can be understood by the following equation, $$\frac{\Delta f_0}{f_0} \cong \frac{A}{2Lk_{fork}} \Delta E \qquad (1)$$

where L, A and E are the length, cross sectional area and Young's modulus of the polymer wire, respectively, $k_{fork}$ and $f_0$ are the effective spring constant and resonance frequency of the fork/wire system, and $\Delta f_0$ is the shift of the resonance frequency upon adsorption or binding of an analyte onto the polymer wire.

According to equation (1), for a given AE (due to the interaction of the analyte molecules), short and thick wire generates a larger frequency shift and thus a higher sensitivity. However, a thick wire means the analytes have to diffuse over a longer distance into the wire, which slows down the response time. Thick wires may also introduce more damping and lower the quality factor, which affects accurate determination of the resonance frequency.

Figure 2A:
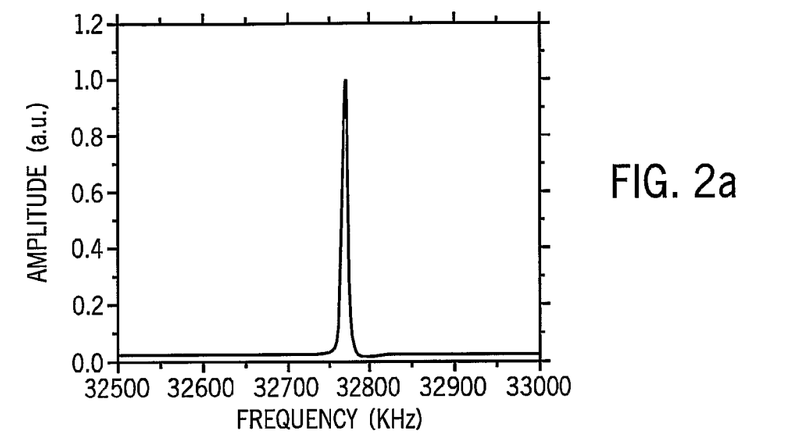
FIG. 2a illustrates the resonance peak of a bare microfabricated quartz tuning fork shown as a function of amplitude and frequency.
Figure 2B:
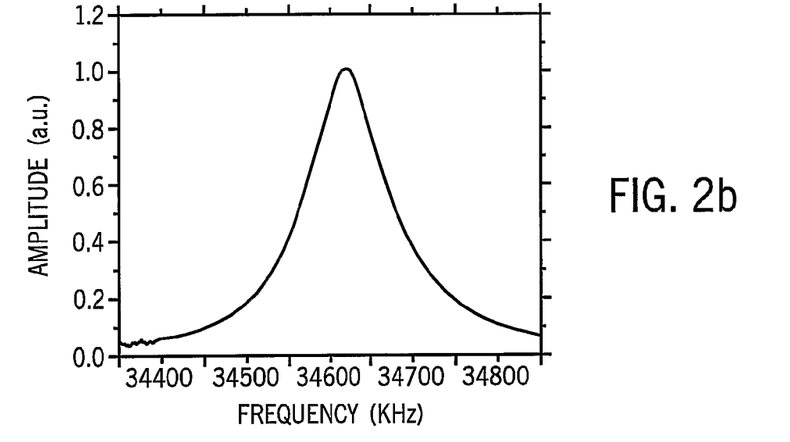
FIG. 2b illustrates the resonance peak of a microfabricated quartz tuning fork with attached polymer wire.

One way to optimize sensitivity and response time is to shorten the length and also decrease the wire thickness. Turning to FIG. 2a, the resonance peak of a bare fork 10 is shown as a function of amplitude and frequency. A typical tuning fork 10 with a resonance frequency of 32.768 kHz has an effective spring constant of approximately 20 kN/m. As would be expected, FIG. 2a shows a peak at approximately 32.768 kHz. FIG. 2b depicts a resonance peak, again as a function of amplitude and frequency, of a fork 10 with attached polymer wire 14. In contrast to the bare fork 10, the resonance peak is considerably broader (Q=300) because of increased damping of the polymer wire 14.

Figure 2C:
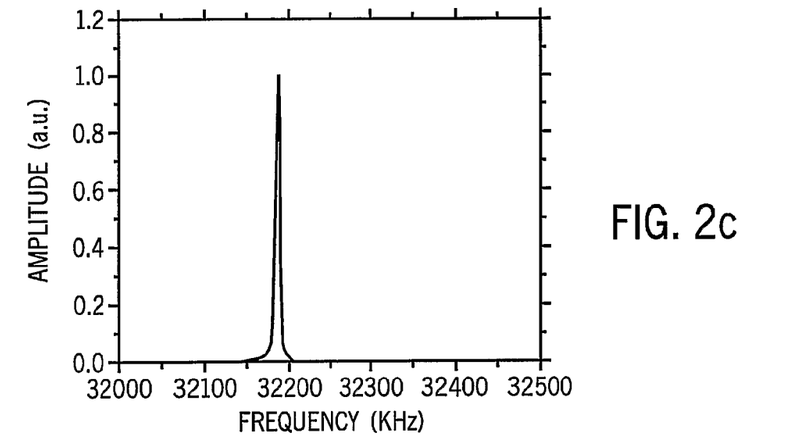
FIG. 2c illustrates the resonance peak of a microfabricated quartz tuning fork with attached polymer wire, the diameter of the wire having been reduced by a focused ion beam (FIB) system.

A polymer wire 14 may be reduced in diameter using a focused ion beam system (FIB). FIG. 2c illustrates a resonance peak of a fork 10 with attached polymer wire 14 in which a small portion of wire 14 has been reduced in diameter to approximately 100 nm×500 nm using a FIB system. The differences in broadness of the resonance peaks of FIGS. 2b and 2c help to demonstrate that use of a thinner polymer wire 14 results in greater sensitivity and response time.

Figure 3A:
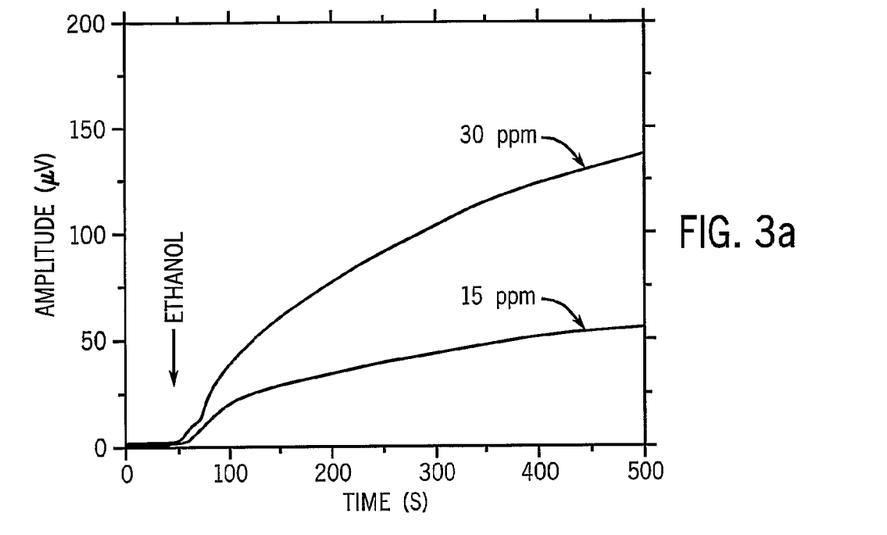
FIG. 3a illustrates the change in oscillation amplitude which results from exposing a polymer wire to ethanol vapor.

To further illustrate the sensitivity and response of a polymer wire to the interaction with an analyte, FIG. 3a shows the change in oscillation amplitude which results from exposing a polymer wire (e.g., ethylcellulose or similar material) 14 to ethanol vapor. FIG. 3a shows the responses of a thick (approximately 15 micrometer) polymer wire upon exposure to 15 and 30 parts-per-million (ppm) of ethanol vapor. The oscillation amplitude changes quickly and then slows down. As would be expected, the change for 30 ppm is quicker and larger than the change for 15 ppm. The small kink in the initial portion of the curves shown is due to disturbance associated with the injection of ethanol into a test chamber. Exposure to ethanol using a bare fork 10 results in no visible changes in oscillation amplitude.

In principle, the adsorption of analytes found in organic vapors can change both the mass and the spring constant of a polymer wire 14. However, the mass of the polymer wire 14 and mass increase due to adsorbed organic vapors is so small as to be negligible. Adsorption of organic vapors, instead, causes a noticeable and measurable change in effective spring constant of the polymer wire 14.

The sensitive dependence of the effective spring constant of a polymer wire 14 can be understood based on the following considerations. As noted previously, when polymer is pulled into a wire 14, the individual polymer chains are forced to align along the pulling direction. After the organic solvent is evaporated, the polymer chains are trapped in this configuration via non-covalent interactions with neighboring polymer chains. When the wire 14 is exposed to an organic vapor, the organic molecules penetrate into the wire and "redissolve" the polymer chains, thus softening the polymer wire.

Figure 3B:
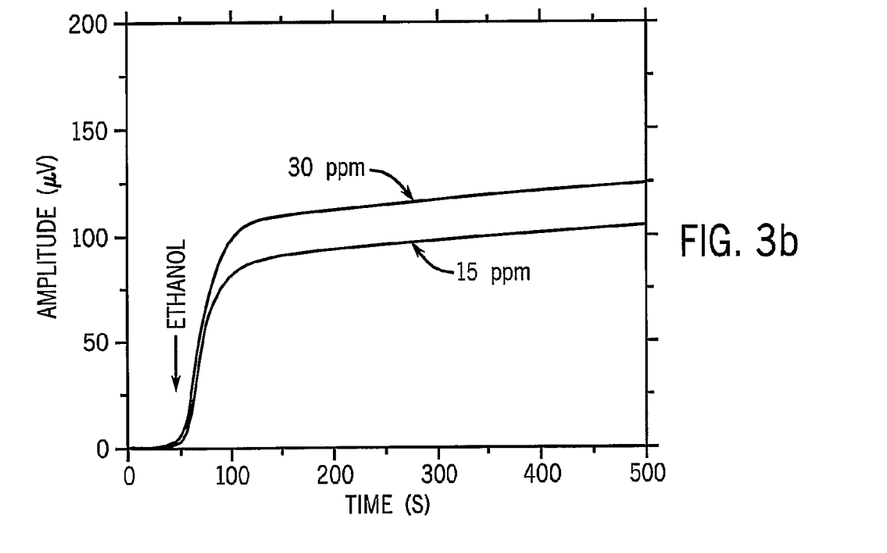
FIG. 3b illustrates the response in oscillation amplitude of an FIB-cut polymer wire upon exposure to ethanol vapor.

As previously discussed, it is possible to further improve the sensitivity and response of a polymer-based sensor device by reducing the diameter of a small portion of wire 14 using an FIB system. FIG. 3b shows the response of the oscillation amplitude of an FIB-cut polymer wire 14 upon exposure of 15 and 30 ppm of ethanol. The amplitude of the FIB-cut polymer wire 14 changes much more sharply upon exposure to an analyte.

Figure 3C:
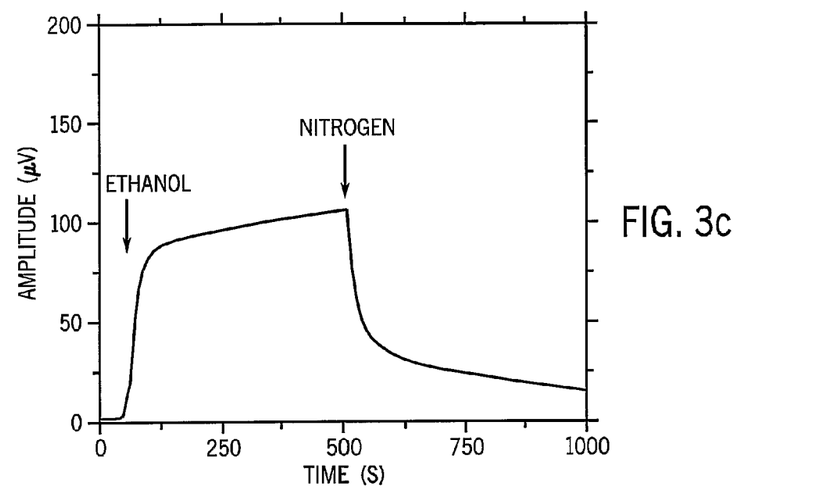
FIG. 3c illustrates the recoverability of a polymer wire to exposure to a chemical analyte.

FIG. 3c demonstrates the recoverability of a polymer wire 14 to exposure to an analyte. As seen in FIGS. 3a and 3b, exposure to ethanol vapor causes a marked change in oscillation amplitude. However, upon removal of the vapor source and, in this case, flushing the polymer wire 14 with nitrogen gas, the oscillation amplitude decreases. Over the course of a few minutes, the polymer wire 14 returns to a previous physical state of the polymer wire.

When a polymer wire 14 is reduced to a single polymer strand, the entire wire is exposed to analyte molecules and the force due to the adsorption or binding of analyte molecules on the polymer strand can be measured with a tuning fork 10. The mechanical stress (force) in the polymer wires 14 induced by the adsorption or binding of analyte molecules can be detected sensitively with a single or an array of quartz crystal tuning forks 10. Since quartz is a piezoelectric material, the fork 10 can be easily driven to oscillate electrically and the small oscillation generates an electrical current (charge or voltage) that can be detected easily and accurately without using optical or other means, which is often referred to as "self-sensing" capability.

Simple and low-noise electronic circuits can be build to drive and detect the resonance of fork 10. In addition, commonly-known methods, such as fitting obtained resonance peaks with Lorentzian functions, can be used to accurately determine frequency shift. The above methods can be implemented with a combination of known hardware and software. The typical uncertainty in a fitted resonance frequency is approximately 0.2 Hz, which leads to a detection limit in the approximately parts-per-billion (ppb) range.

The force detection limit is primarily determined by thermal noise. The thermal noise of a typical quartz tuning fork 10 as a function of force is approximately 5 pN/$\sqrt{\text{Hz}}$ (varies as $1/\sqrt{Q}$). For a bandwidth of 1 Hz (1 s response), a few pN of force can be detected. Considering that the force to break a carbon-carbon bond is a several nN, three orders of magnitude greater, the force sensitivity of fork 10 can detect a very small change in the sensing wires 14.

In comparison to commonly-used quartz forks 10, piezoresistive microfabricated cantilevers, discussed previously, can also have self-sensing ability. Thin film-based piezoelectric sensors can have higher piezoelectric constants than quartz. However, thin film-based piezoelectric devices have much higher energy dissipation. As a result, thin film-based piezoelectric devices consume much greater power than quartz tuning forks 10. Additional energy will be consumed when the resistance is constantly measured.

The power consumption of an oscillator is given by $$P = \pi f_0 k_{fork} A^2 / Q, \qquad (2)$$

where A is the oscillation amplitude. In contrast to piezoresistive cantilevers, for a fork 10 having parameters of Q=8000, $k_{fork}$=40 kN/m, resonance frequency ($f_0$) 32 kHz and amplitude 100 nm, power consumption can be calculated to be 48 pW. Actual power consumption of fork 10 is likely due to signal processing. The low power dissipation in quartz tuning forks 10 is the reason that the battery in an ordinary wristwatch can last for years.

As mentioned previously, a fork 10 based sensor can be operated using a single tuning fork 10 or an array of forks 10 on which different wires are attached. Utilization of an array of forks 10 is particularly suitable for simultaneous detection of a range of different chemicals or for improving the detection specificity of a particular chemical species. The array approach also allows for the use of one or several tuning forks as a reference to minimize signal drift due to changes in humidity and temperature.

Figure 4:
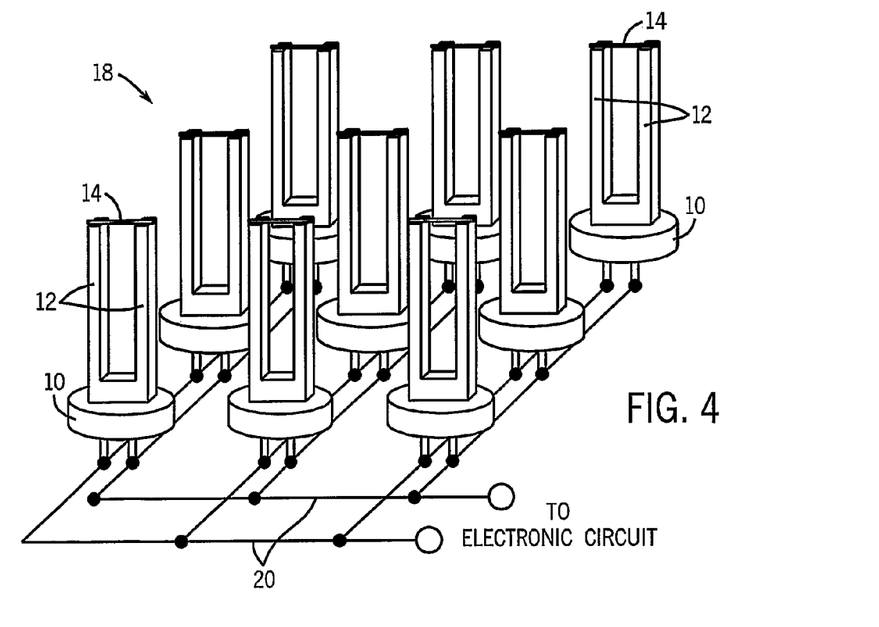
FIG. 4 illustrates an array of devices for sensing a chemical analyte.

Turning to FIG. 4, an array 18 of multiple forks 10 is seen. Again, the respective prongs 12 of each fork 10 are shown, with a wire 14 attached or coupled to the upper end of each prong 12. Electrical wire 20 is shown which connects every fork 10 in the array 18 to an electronic circuit.

Array 18 can be used to more accurately detect polar chemical vapors, such as ethanol, which are more challenging to detect than non-polar chemicals because of the interference of a large amount of water vapor in ambient air. A fork 10 can be devoted to monitor relative humidity and other forks 10 can include wires 14 made of polymers with different affinity to the polar chemical vapor.

Array 18 can contain a variety of forks 10 which have varying types of wires 14 which have been fabricated to detect a specific analyte or combination of analytes. For example, an array 18 may have a fork 10 with accompanying polymer wire 14 which has been designed and calibrated to detect nitroethylbenzene, a substance commonly used in TNT and other explosives. Array 18 may also have a fork 10 with accompanying polymer wire 14 which has been designed and calibrated to detect arsenic, a commonly used poison. Additionally, array 18 may have a fork 19 with accompanying polymer wire 14 which has been designed and calibrated to detect high levels of lead. By using various combinations of specifically designed and calibrated forks 10 in array 18, a single sensor may have the ability to detect a wide range of analytes or combinations of analytes. An array 18 of forks 10 can also serve to provide additional redundancy and improve confidence in a reading by ensuring that the correct analyte has been detected.

The resonance of a fork 10 in array 18 can be measured in two ways. The first way is to measure the amplitude by scanning the frequency within a certain range so that the individual forks 10 with different resonance frequencies can be set to resonate one by one. The scan rate determines how fast one can detect analytes. The second approach is to simultaneously drive all the forks 10 to resonance using noise with an accompanying bandwidth which spans the resonance frequencies of all forks 10 in array 18. Simultaneously driving all forks 10 in array 18 to resonance gives quick response, but consumes more power.

Figure 5:
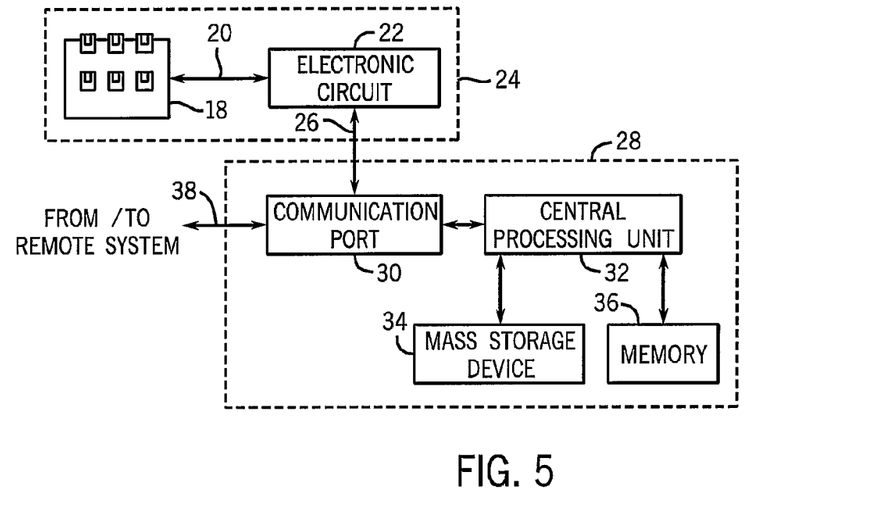
FIG. 5 illustrates a chemical analyte detection system.

Turning to FIG. 5, a block diagram of a possible detection device and system is shown. Array 18 is again shown, connected by electrical wires 20 to electronic circuit 22. Local controller 24 can encompass array 18, wires 20 and electronic circuit 22. Electronic circuit 22 may be manufactured or supplied as an integrated or separate component from array 18. Electronic circuit 22 can be composed of a variety of interrelated electrical components such as resistors, capacitors and transistors which are integrated into a printed circuit board (PCB) or similar technology. Array 18 can be designed to simply plug into a PCB or related electronic component. Local sensor device 24 may include such integrated electronic components as amplifiers or filters which are located as part of electronic circuit 22. Electronic circuit 22 can have integrated electronic components described above which are embedded in conventional microchip or similar technology.

In one embodiment, an AC modulation may be used to drive array 18 into resonance. The electrical outputs of array 18 can be amplified with a current amplifier located as part of electronic circuit 22. The output of the current amplifier can then be sent to a lock-in amplifier, also located as part of electronic circuit 22. The frequency of the AC modulation can be linearly swept within a range that covers the resonance frequencies of all the forks 10 in array 18. The output from the lock-in amplifier may be recorded as a function of frequency with sufficient resolution to provide a spectrum of the entire array 18.

Local controller 24 can include a power supply such as a battery in order to drive array 18 into resonance and supply power to amplify, filter, or otherwise analyze the electrical outputs of array 18. The power supply can be located as part of electronic circuit 22 or elsewhere on local controller 24.

Referring again to FIG. 5, electronic circuit 22 can send or receive electrical signals or other communication information through link 26 to a larger system 28. System 28 can be a workstation, desktop, notebook, PDA or other computer. System 28 includes communication port 30 which receives information and/or electrical signals from electronic circuit 22. System 28 can also include central processing unit 32, mass storage device 34 and memory 36. System 28 can have associated software which translates incoming raw electrical signals or information passed through link 26 into manageable information which is displayed or seen on a graphical user interface (GUI) or similar device. System 28 may pass raw or processed electrical signals or information through link 38 to an external system for viewing or further processing.

Local controller 24 may be integral to system 28, or can be external to system 28. Electronic circuit 22 located on local controller 24 may include electrical components necessary to convert electrical signals to radio frequencies. Link 26 can, in turn, be a wireless connection between system 28 and local controller 24, such as IEEE 802.11a/b/g wireless protocols or equivalent. Local controller 24 can include a hand-held or wrist-worn device such as a wristwatch.

In an example of using local controller 24 and system 28, a user may place local controller 24 on his wrist. Local controller 24 can include array 18 which has forks 10 and accompanying wires 14 which have been selected, designed and calibrated to identify chemical analytes of chemicals known to be present in and around explosives. A user may wear local controller 24 as part of the user's occupation, where local controller 24 is continually powered and constantly monitoring the air, such as a customs officer who inspects arriving goods.

Local controller 24 may have onboard memory as part of the individual components of electronic circuit 22. When a change in resonant frequency, amplitude or quality factor is determined by local controller 24, associated software located on local controller 24 can check the frequency response against a library or database located in the onboard memory of local controller 24. When a match is detected, an alarm can be triggered. Similarly, local controller 24 can communicate wirelessly with system 28 through link 26 to provide, for example, a daily summary of any trigger events. The trigger events can be logged by system 28 or transmitted to an external system through link 38 for further analysis. System 28 can include onboard software which can log trigger events as described, analyze a frequency response or determine a change in amplitude. The onboard software can be adapted to efficiently determine frequency shifts or amplitude changes for a particular use, environment and type or groups of analytes to be detected. The onboard software can be commercially obtained and can include algorithms and methods generally known in the art.

While one or more embodiments of the present invention have been illustrated in detail, the skilled artisan will appreciate that modifications and adaptations to those embodiments may be made without departing from the scope of the present invention as set forth in the following claims.

What is claimed is:

1. A device for sensing a chemical analyte, comprising:
   at least one tuning fork having first and second prongs and having an associated resonant frequency; and
   a wire attached to the tips of the first and second prongs such that it bridges the gap between the first and second prongs of the at least one tuning fork, wherein the wire consists essentially of at least one strand and wherein the analyte interacts with the wire and causes a change in the resonant frequency of the at least one tuning fork such that the wire is stretched and compressed when the at least one tuning fork oscillates.

2. The device of claim 1, wherein the at least one tuning fork is comprised of quartz.

3. The device of claim 1, wherein the at least one tuning fork comprises a plurality of tuning forks, each having a wire attached to the tips of the first and second prongs such that it bridges the gap between the first and second prongs of each of the plurality of tuning forks, where the plurality of tuning forks is arranged in an array to provide a redundancy of measurement or to detect a plurality of analytes.

4. The device of claim 1, wherein the wire is selected from an available plurality of polymers based on a response of the wire to the analyte.

5. The device of claim 1 wherein the associated resonant frequency has a peak around 32.768 kHz.

6. The device of claim 1 wherein the at least one tuning fork is polymerized to interact with the analyte.

7. The device of claim 1, further including an electronic circuit coupled to the at least one tuning fork to measure the change in the mechanical property of the tuning fork.

* * * * *